United States Patent [19]

Evans, III

[11] Patent Number: 4,724,846

[45] Date of Patent: Feb. 16, 1988

[54] CATHETER GUIDE WIRE ASSEMBLY

[75] Inventor: Russell M. Evans, III, Lower Burrell, Pa.

[73] Assignee: Medrad, Inc., Pittsburgh, Pa.

[21] Appl. No.: 817,580

[22] Filed: Jan. 10, 1986

[51] Int. Cl.⁴ .......................... A61B 5/00; A61M 25/00
[52] U.S. Cl. .................................. 128/772; 128/657; 604/95
[58] Field of Search .................... 604/95, 170, 280; 128/656–658, 772, 341–344, 348.1

[56] References Cited

U.S. PATENT DOCUMENTS

| | | | |
|---|---|---|---|
| 3,906,938 | 9/1975 | Fleishhacker | 128/772 |
| 4,003,369 | 1/1977 | Heilman et al. | 128/772 |
| 4,538,622 | 9/1985 | Sampson et al. | 128/657 X |
| 4,554,929 | 11/1985 | Samson et al. | 128/772 |
| 4,616,653 | 10/1986 | Samson et al. | 604/95 X |
| 4,619,274 | 10/1986 | Morrison | 604/170 X |

*Primary Examiner*—Dalton L. Truluck
*Attorney, Agent, or Firm*—Fleit, Jacobson, Cohn & Price

[57] ABSTRACT

A catheter guide wire assembly for use in angioplasty. The assembly has a combined core and safety wire extending longitudinally between its proximal and distal ends. A wound wire is positioned around the combined core and safety wire and follows the contour thereof. The combined core and safety wire has a relatively short and relatively flexible distal end portion with a first diameter, an elongated, relatively rigid proximal body portion having a diameter greater than the first diameter, and a tapered intermediate portion interconnecting the distal end portion and the proximal body portion. Ends of the wire and the combined core and safety wire are rigidly connected to each other. The guide wire assembly guides and supports a balloon catheter used to dilate a stenosis region of a blood vessel. Since the distal end has a reduced diameter, the distal end can be left within the stenosis region during the performance of a fluoroscopic process used to ascertain whether or not the stenosis region has been adequately enlarged by a dilatation procedure.

10 Claims, 3 Drawing Figures

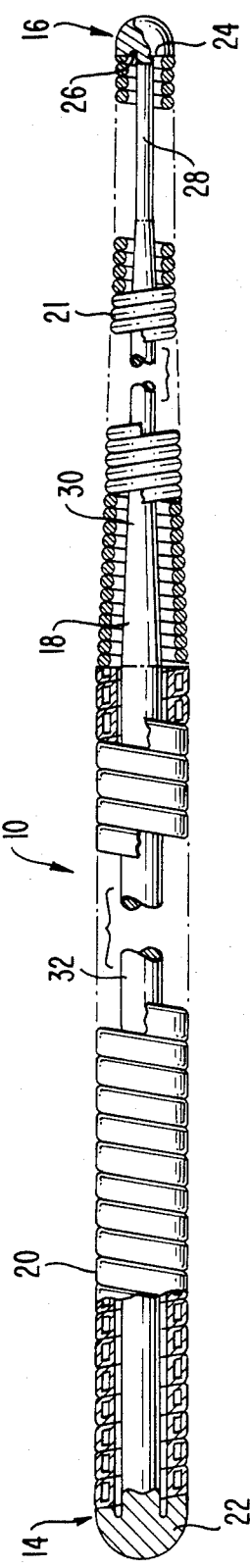
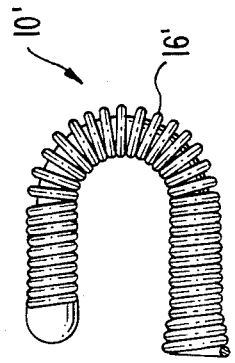
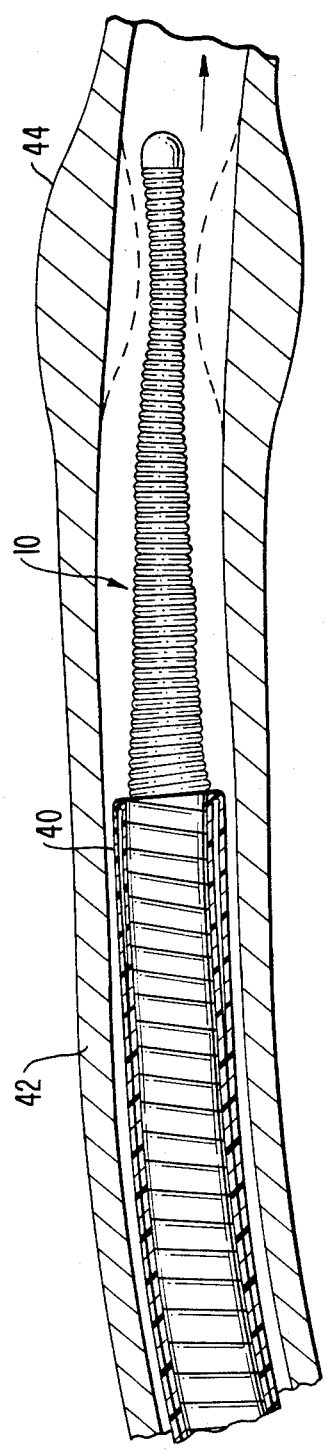

CATHETER GUIDE WIRE ASSEMBLY

BACKGROUND OF THE INVENTION

1. Field of the Invention

The present invention relates to catheters, and more particularly, to catheter guide wire assemblies having a coiled wire wrapped round a core and safety wire.

2. Description of the Prior Art

Current techniques of introducing a catheter into the vascular system of a patient include the following steps: insertion of a sharp cannula through the skin and into the vascular system, insertion of a spring guide wire through the cannula and into the vascular system, removal of the cannula from the patient's body, and insertion of the catheter into the body by sliding the catheter over the guide wire. The guide wire is then withdrawn, and the catheter is ready for further positioning and use, or the guide wire can be left in position during use of the catheter.

It should be evident that the guide wire must be flexible and yet strong. It must be flexible enough to negotiate the desired tortuous path of the vascular system and do no damage with its leading tip portion and yet be strong enough to resist doubling back, kinking or breaking during the insertion and retraction procedures. It is accordingly desirable that the guide wire have a flexible and yet guidable distal tip, and a relatively stiff, strong elongated body portion. In addition to the foregoing, the guide wire should have an ultra-smooth outer surface.

A guide wire, sometimes referred to as a spring guide, is constructed of a finely wound spring with one or more wires running longitudinally within the spring's central lumen. A guide wire having a wound outer casing with an ultra-smooth surface, and an integral safety-core wire for ensuring structural integrity of the guide wire, without impairing guide wire flexibility at the distal tip, and a method of manufacturing such guide wire are described in U.S. Pat. No. 4,003,369, entitled "Angioplasty Guidewire With Safety Core Wire," the contents of which are herein incorporated by reference.

In one embodiment of the guide wire described in the referenced patent, the ultra-smooth outer surface of the wound guide wire is developed by coating a base flat-wire with a lubricating agent, such as TEFLON synthetic resin, prior to being spring-wound about a core wire. In this manner, flaking of the outer coating is minimized during bending of the guide wire when in use. In another embodiment, the surface is smoothed by first lightly grinding the surface of the spring-wound flatwire by abrasion, and subsequently electropolishing the guide wire surface.

A safety-core extends longitudinally through the outer casing formed by the wound guide wire and is attached to the casing at the distal and proximal ends. The outer casing has a substantially uniform diameter throughout its entire length. The distal tip of the safety wire is made ultra-flexible in one direction by flattening a circular wire and immersing the wire into an electro-etching solution. Withdrawing the safety wire from the etch at a predetermined rate produces a uniformly tapered distal tip for the safety wire. In this manner, the transition between the ultra-flexible flattened distal tip and the relatively rigid circular body is smooth and uniform, having a carefully controlled cross-sectional area. Therefore, the possibility of breaking or kinking is minimized. That is, locations of preferential bending are eliminated.

For angioplasty or arterial dilatation, the guide wire is inserted into the blood vessel to be treated and a balloon catheter supported by the guide wire is positioned so that a distensible portion of the catheter is located in the stenosis to be treated. The catheter is then pressurized so that the distensible portion expands and compresses the stenosis. The balloon catheter is then deflated and the guide wire and catheter are pulled back from the portion of the blood vessel containing the stenosis so that a contrast medium used in a fluoroscopical procedure can be introduced into the blood vessel. Flow of the contrast medium through the region containing the stenosis is sensed to determine if the expanded stenosis has returned to its original restricted condition. If the dilatation procedure has not been successful, the guide wire must then be passed back through the stenosis a second time so that the dilatation procedure can be repeated. It should be appreciated that the reinsertion of the guide wire through the stenosis can be quite risky because of the just completed attempt to compress the stenosis. If it is necessary to repeat the process several times, the risk can become significant.

SUMMARY OF THE INVENTION

Accordingly, it is an object of the present invention to provide an improved guide wire assembly that does not require removal of the entire guide wire assembly from the region of the blood vessel containing the stenosis in order to perform a fluoroscopic procedure.

Like the guide wire described in the aforementioned U.S. Pat. No. 4,003,369, the guide wire assembly provided by the present invention has an integral safety-core wire, which is relatively rigid in the major portion of its length and has a flexible distal tip. While the guide wire described in the patent has a substantially uniform outer diameter throughout its entire length, the guide wire assembly provided by the present invention has a distal end region with a reduced outer diameter so that the end region provides minimum interference to blood flow. As a result, the end region can be positioned in a portion of a blood vessel containing a stenosis, without significantly interfering with the performance of a fluoroscopic procedure.

Considering the present invention in more detail, it provides a catheter guide wire assembly having an elongated proximal body portion and a distal end portion. A combined core and safety wire extends longitudinally between the proximal and distal ends of the assembly and has a relatively short and relatively flexible distal end portion with a first diameter, an elongated, relatively rigid proximal body portion having a diameter greater than the first diameter, and a tapered intermediate portion interconnecting the distal end portion and the proximal body portion. A wire is wound and is positioned around the combined core and safety wire and basically follows the contour thereof so that the assembly has a distal end portion with an external diameter less than the external diameter of the elongated proximal body portion. Respective ends of the wire are rigidly interconnected, for instance by welding, with proximal and distal end portions of the combined core and safety wire.

Preferably, the distal end portion of the combined core and safety wire has a uniform diameter portion extending forwardly from the intermediate portion and an outermost end region formed as a paddle. The paddle gives the assembly greater strength by absorbing heat during welding of the wire to the end region.

Preferably, the wound wire around the combined core and safety wire has a portion encompassing the elongated proximal body portion that has a generally rectangular cross section so that the assembly has a substantially cylindrical peripheral surface. Such surface facilitates passage of the cylindrical catheter guide wire assembly through a blood vessel. The portion of the wire wound round and covering the distal end and the intermediate portion has a smaller cross-sectional area so that the external diameter of the distal end of the guide wire assembly is reduced.

Objects of the present invention, as well as many of the attendant advantages thereof, will become more readily apparent when reference is made to the following description, when taken in conjunction with the accompanying drawings.

BRIEF DESCRIPTION OF THE DRAWINGS

In the detailed description of the preferred embodiments of the invention hereinafter presented, reference is made to the accompanying drawings, in which:

FIG. 1 is a plan view, partially in section, of one embodiment of a catheter guide wire assembly according to the present invention;

FIG. 2 is a plan view of a modification of a portion of the guide wire assembly of FIG. 1; and FIG. 3 is a schematic view illustrating the guide wire assembly of FIG. 1 during a portion of a dilating procedure.

DESCRIPTION OF THE PREFERRED EMBODIMENTS

The present description will be directed in particular to elements forming part of, or cooperating more directly with, the present invention. Elements not specifically shown or described herein are understood to be selectable from those known in the art.

Referring now to the drawings, and to FIG. 1 in particular, an embodiment of a catheter guide wire assembly according to the present invention, generally designated 10, is illustrated.

An elongated guide wire assembly 10, constructed in accordance with the teachings of the present invention, comprises an elongated body with a proximal portion 14 and a distal tip portion 16. A combined core and safety wire 18 extends from the proximal end 14 to the distal end 16 of the guide wire assembly 10. The external body of the guide wire assembly 10 takes the form of a coil spring, and is developed from a wound wire, such as a flat wire. One coil formed from the flat wire is indicated at 20. Preferably, the wire forming the external body is a composite wire and has a second portion formed from wound wire, one coil of which is indicated at 21. The safety core wire 18 is welded, or in some other fashion, connected to the respective ends of the wound body of the guide wire, as shown at 22 and 24. Preferably, the distal end of the combined core and safety wire 18 is shaped to form an annealing paddle 26 so that the assembly is given greater strength because the paddle absorbs heat generated during welding to interconnect the coiled wire with the tip.

The combined core and safety wire 18 comprises the essentially flat, expanded distal tip portion or paddle 26, a uniform diameter flexible portion 28 extending rearwardly from the tip portion 26 and combining therewith to form a relatively short and relatively flexible distal end portion of the member 18. A smoothly tapering transition or intermediate portion or region 30 extends between the portion 28 and a relatively long and relatively rigid proximal body portion 32. The result is a guide wire assembly having an extremely flexible distal, or leading tip, a transition region gradually increasing in stiffness, and a stiff elongated shank suitable for use as a core wire to add stiffness to an associated guide wire casing. The safety core wire 18 is welded to the guide wire casing at both its proximal and distal ends.

As a result, the assembly 10 has a distal end portion 16 with a high degree of flexibility so that the assembly can easily follow the tortuous path of the human vascular system. At the same time, the proximal elongate body region 14 is less flexible, and capable of adding necessary stiffness for propelling the guide wire assembly through the vascular system. Becasuse of the gradual transition provided by region 30 between the parts 28 and 32 of the member 18, regions of preferential bending and breaking are eliminated.

In one embodiment of the present invention, the portion 32 has an external diameter of 0.018 inches and a length of approximately 140 cm. The coil 20 covering this portion of the assembly has a cross-sectional area of approximately 0.006 ×0.0126 inches. Preferably, a coating of TEFLON synthetic resin is applied to the wire to facilitate its passage through a blood vessel. In this embodiment, the distal end portion 16 has a part extending rearwardly from the leading tip that has a uniform external diameter of approximately 0.021 inches and a length of between 2.0 and 5.0 cm (0.787 to 1.968 inches). The portions 28 and 30 have a combined length of between approximately 7.0 and 13.0 cm (2.756 to 5.118 inches) and are encompassed with a round wire having a diameter of approximately 0.004 inches. Preferably, the core wire or member 18 is plasma welded to the spring coil wire, without the addition of filler material. The ends of the assembly are then ground, as necessary, and the tips polished.

Referring now to FIG. 2, a modification of the embodiment of FIG. 1 is illustrated. The same reference numerals, with primes attached, have been used to identify elements similar to those previously described.

Although the distal tip 16 of the assembly 10 is relatively flexible, it can still dislodge plaque buildup in blood vessel during passage of the assembly though a stenosis. To minimize this possibility, a guide wire assembly 10', as illustrated in FIG. 2, is formed with a curved distal end, or J-tip 16'. The J-tip 16' provides a blunt, minimum-trauma, distal tip which helps prevent the guide from digging into plaque deposits. The J-tip 16' tends to "bounce" around the stenosis region, without digging into the plaque, to facilitate centering of the assembly during its insertion through the stenosis region of the blood vessel.

Referring now to FIG. 3, use of the assembly 10 during an angioplasty procedure is illustrated. As illustrated, the assembly 10 provides support for an angiocatheter 40 during its passage through a blood vessel 42. The vessel 42 has a stenosis region 44 where blood flow, in the direction of the arrow, is restricted. Initially, the assembly 10, together with the catheter 40, is inserted into the blood vessel to be dilated. The relatively flexible end region 16 facilitates guiding of the assembly through the tortuous blood vessel, while the elongated relatively rigid portion 14 provides sufficient strength for advancing the assembly through the vessel.

The assembly 10 is inserted into the vessel 42 to position a distensible portion of the catheter 40 in the region 44 of the stenosis. The distensible portion is then inflated to compress the fatty deposits or plaque forming the stenosis. After the balloon catheter is depressurized, the stenosis region ideally will assume the shape shown in solid lines in FIG. 3. Unfortunately, some buildups are not fibrous, or tough, but are more like an elastic sponge, that is, the buildups tend to return to their original shapes, as illustrated in dotted lines in FIG. 3. Or, the deposits may be only partially compressed. Thus, a fluoroscopic procedure is used to determine if the stenosis has been successfully treated. During the fluoroscopic procedure, a radiopaque substance is injected into the blood stream and its passage through the stenosis region is monitored to determine if the lumen in the region has been sufficiently expanded.

With previously known guide wire assemblies, it was necessary to remove the entire assembly from the region of stenosis prior to performing the fluoroscopic procedure because the possibility existed that fluid flow through the vessel would be blocked by contact between the portions of the blood vessel forming the stenosis and external surfaces of the guide wire assembly. After the assembly had been removed and fluoroscopy had determined that the dilatation procedure had not provided adequate results, it was then necessary to reposition the distensible portion of the catheter 40 in the stenosis region.

With the present invention, the requirement to displace the entire assembly from the stenosis region has been eliminated because there is sufficient clearance between the reduced diameter distal region and portions of the sidewall of the vessel forming the stenosis. As illustrated in FIG. 3, sufficient clearance is provided between the stenosis, as illustrated in dashed lines, and the distal portion of the assembly 10 that a fluoroscopic procedure can be performed while the distal end is still positioned in the region 44. Thus, should it be necessary to reposition the catheter 40 in the region 44, it is relatively easy to guide the enlarged diameter portion of assembly 10 back through the stenosis to properly locate the catheter for a second or subsequent dilatation.

Various modifications of the present invention are contemplated. For instance, the combined core and safety wire can be integrally formed and provide the only rigid connection between the ends 14 and 16. Alternatively, an additional safety wire can extend the length of the assembly 10 to ensure that the components of the assembly can be removed from the vessel upon the completion of an angioplasty procedure or arterial dilatation. Also, the round wire forming the coils 21 can be used to encompass the entire member 18. Such procedure, however, would be time consuming and require a larger quantity of wire than that required with the use of a composite wound wire.

Accordingly, it should be appreciated that the embodiments of the present invention previously described are for the purposes of illustration only, and are in no way intended to be limited. Rather, it is the intention that the present invention be limited only as defined in the appended claims.

What is claimed is:

1. A catheter guide wire assembly having an elongated proximal body portion and a distal end portion comprising;
   (a) a combined core and safety wire extending longitudinally between proximal and distal ends of the assembly and having:
      (1) a relatively short and relatively flexible distal end portion having a first diameter,
      (2) an elongated, relatively rigid proximal body portion having a diameter greater than said first diameter, and
      (3) a tapered intermediate portion interconnecting the distal end portion and the proximal body portion;
   (b) a wire wound around the combined core and safety wire and being contoured to follow the contour of said core and safety wire so that the assembly has a distal end portion with an external diameter less than the external diameter of the elongated proximal body portion; and
   (c) means for connecting respective ends of the wound wire to proximal and distal end portions of said combined core and safety wire.

2. A catheter guide wire assembly according to claim 1, wherein said distal end portion of said combined core and safety wire has an outermost end region formed as a paddle to facilitate interconnection between said wire and said combined core and safety wire.

3. A catheter guide wire assembly according to claim 1, wherein said distal end portion of said combined core and safety wire has a uniform diameter portion extending from the intermediate portion towards the distal end of said assembly, the uniform diameter being said first diameter.

4. A catheter guide wire assembly according to claim 1, wherein said wire is a composite wire having a first portion with a generally rectangular cross section encompassing said proximal body portion of said combined core and safety wire and a second portion having a cross-sectional area smaller than said first portion encompassing said distal end and said intermediate portions of said combined core and safety wire.

5. A catheter guide wire assembly according to claim 3, wherein the length of said uniform diameter portion is not more than 5.0 cm.

6. A catheter guide wire assembly according to claim 5, wherein said first diameter is approximately 0.021 inches.

7. A catheter guide wire assembly according to claim 6, wherein the diameter of said proximal body portion of said combined core and safety wire is approximately 0.035 inches.

8. A catheter guide wire assembly according to claim 7, wherein the length of said elongated proximal body portion of said combined core and safety wire is at least ten times the combined lengths of said distal end and said intermediate portions.

9. A catheter guide wire assembly having an elongated proximal body portion and a distal end portion comprising:
   (a) a core wire extending longitudinally between proximal and distal ends of the assembly and having a distal end portion of smaller diameter as compared with a proximal portion thereof;
   (b) a wound wire around the core wire, said wound wire having an external diameter at its distal end portion that is less than the external diameter at its proximal body portion and being contoured to follow the contour of said core wire; and (c) means for connecting respective ends of the wound wire to proximal and distal end portions of said core wire.

10. A catheter guide wire assembly having an elongated proximal body portion and a distal end portion comprising:
(a) a core wire extending longitudinally between proximal and distal ends of the assembly and having a distal end portion of smaller diameter as compared with a proximal portion thereof;
(b) a wound wire around the core wire, said wound wire having an external diameter at its distal end portion that is less than the external diameter at its proximal body portion, the wire of said wound wire having a substantially circular cross-sectional area, said wound wire having an outer contour matching the contour of said core wire; and
(c) means for connecting respective ends of the wound wire to proximal and distal end portions of said core wire.

* * * * *